US00PP31506P2

(12) United States Plant Patent
Cain

(10) Patent No.: US PP31,506 P2
(45) Date of Patent: Mar. 3, 2020

(54) GRAPEVINE PLANT NAMED 'IFG FORTY'

(50) Latin Name: ***Vitis interspecific* hybrid**
Varietal Denomination: IFG Forty

(71) Applicant: David Cain, Bakersfield, CA (US)

(72) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 0 days.

(21) Appl. No.: 16/501,162

(22) Filed: Mar. 4, 2019

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 5/0812
See application file for complete search history.

*Primary Examiner* — Kent L Bell

(57) ABSTRACT

This invention is a new and distinct grapevine variety denominated 'IFG Forty'. The new grapevine is characterized by producing naturally large seedless black berries having an elliptic shape with a mild labrusca flavor. Fruits are medium in acidity, with a firm texture and have excellent eating quality.

1 Drawing Sheet

Latin name of the genus and species claimed: *Vitis interspecific* hybrid.

Variety denomination: 'IFG Forty'.

BACKGROUND OF THE INVENTION

The new and distinct grapevine described and claimed herein originated from hand a pollinated cross of the interspecific variety 'Arkansas 2798' (unpatented) and '01170-042-232' (unnamed *Vitis vinifera* selection from the IFG breeding program), hybridized in May 2008. The abortive seed traces were subsequently embryo cultured and the resulting 19 plants were planted in the field in April 2007. The present variety of grapevine was selected as a single plant in August 2008 and was first asexually propagated by hardwood cuttings in December 2008 near Delano, Kern County, Calif. These resulting cuttings produced second generation plants that were planted during April 2009 near Delano, Kern County, Calif. and were observed for four years and found to reproduce true-to-type.

BRIEF SUMMARY OF THE INVENTION

The new grapevine 'IFG Forty' is characterized by producing naturally large seedless black berries having an elliptic shape with a mild labrusca flavor. Fruits are medium in acidity, with a firm texture and have excellent eating quality. Berries color readily even in hot climatic conditions and produce completely colored black berries. Vines are productive and can be pruned to short spurs. Clusters are medium to large size.

'IFG Forty' can be distinguished from its maternal parent, the 'Arkansas 2798', by having larger berry and cluster size, having a more completely black color, by not being as prone to berry splitting and by having a milder labrusca flavor.

The new grapevine differs from its pollen parent the '01170-042-232' by having black rather than dark red berry color, by having an elliptic rather than round to oval berry shape, by having much larger natural berry size, by having a larger, looser cluster, and firmer berries.

'IFG Forty' is most similar to 'Autumn Royal' (non-patented). It differs from 'Autumn Royal' by having softer textured berries with smaller residual seed traces, by ripening approximately three weeks earlier, and by having a mild labrusca flavor.

'IFG Forty' is somewhat similar to 'IFG Twenty' (U.S. Pat. No. 26,799). 'IFG Forty' differs from 'IFG Twenty' by having an elliptic rather than narrow ellipsoidal berry shape, by having smaller residual seed traces, by having a looser cluster form and by ripening earlier.

BRIEF DESCRIPTION OF THE DRAWING

The accompanying photographic drawing in FIG. 1 illustrates in full color 'IFG Forty'. The photograph was taken outdoors with indirect lighting. The colors are as nearly true as is reasonably possible in a color representation of this type. The left side of the drawing has a typical berry in cross section and a mature leaf. A mature fruit cluster is represented in the center of the drawing. The right side of the drawing has a young shoot tip with tendrils and young leaves.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Forty' plants grown in the vicinity of Delano, Kern County, Calif. during 2011 and 2012, and is believed to apply to plants of the variety grown under similar conditions of soil and climate elsewhere:

VINE

General:

*Vigor*.—Vigorous.
*Density of foliage*.—Dense.
*Productivity*.—Very productive, producing about 25.8 to 38.7 kg of fruit per vine.
*Root stock*.—Own root.
*Training method*.—Typically spur pruned leaving 2 bud spurs.

Trunk:

*Trunk diameter of* 4-*year-old vines at* 30 *cm above the soil line*.—About 4.5 cm.
*Shape*.—Medium stocky.
*Straps*.—Short — split.
*Surface texture*.—Medium rough texture.
*Inner bark color*.—The following colors were observed: Greyed-orange: 174A and 175C and 175D.

SHOOTS

Young shoot:

*Form of tip*.—Fully opened.
*Distribution of anthocyanin coloration of tip*.—Absent.
*Intensity of anthocyanin coloration of tip*.—Absent.
*Density of prostrate hairs on tip*.—Sparse to medium.
*Density of erect hairs on tip*.—Very sparse.
*Color*.—The following colors were observed: Yellow-green: 144A and 144B and 146A.

Woody shoot (mature canes):

*Internode length*.—Medium: About 7.2 cm.
*Width at node*.—About 1.0 cm.
*Cross section*.—Circular.
*Surface*.—Striate.
*Main color*.—The following colors were observed: Greyed-orange; 164A and 164B and 164C and 164D.
*Density of erect hairs on nodes*.—None or very sparse.
*Density of erect hairs on internodes*.—None or very sparse.
*Axillary shoot vigor at full bloom*.—Strong: Approximately 23.5 cm long.

Flowering shoot:

*Vigor during flowering*.—Moderate.
*Attitude during flowering on shoots not tied*.—Semi-erect.
*Color*.—Dorsal side of internodes — Yellow-green: 146C, with Red-purple stripes: 59B.
*Color*.—Ventral side of internodes — Yellow-green: 146C.
*Color*.—Dorsal side of nodes — Yellow-green: 146C.
*Color*.—Ventral side of nodes — Yellow-green: 146C.
*Density of prostrate hairs of nodes*.—None.
*Density of erect hairs of nodes*.—None.
*Density of prostrate hairs on internode*.—None.
*Density of erect hairs on internode*.—None.
*Anthocyanin coloration of buds*.—Absent.

Tendrils:

*Distribution on the shoot* (*at full flowering*).—Discontinuous.
*Length of tendril*.—Long: About 22.8 cm.
*Thickness of tendril* 2 *cm from base*.—About 1.7 mm.
*Color*.—The following colors were observed: Yellow-green; N144A and N144B and N144C, and 145A.
*Form*.—Bifurcated and trifurcated.
*Number of consecutive tendrils*.—2.

LEAVES

Young leaves:

*Color of upper surface of first four distal unfolded leaves*.—Yellow-green: 146C.
*Average intensity of anthocyanin coloration of six distal leaves prior to flowering*.—Weak.
*Density of prostrate hairs between veins* (*lower surface*).—Very sparse.
*Density of prostrate hairs on veins* (*lower surface*).—Sparse.
*Density of erect hairs between veins* (*lower surface*).—Absent.
*Density of erect hairs on veins* (*lower surface*).—Very sparse.

Mature leaves:

*Average length*.—About 15.3 cm.
*Average width*.—About 17.6 cm.
*Mature leaf size*.—Medium large.
*Shape of blade*.—Wedge-shaped.
*Number of lobes*.—5.
*Blade venation*.—Palmate.
*Anthocyanin coloration of main veins on upper side of blade*.—Weak to medium.
*Mature leaf profile*.—Undulate.
*Blistering surface of blade upper surface*.—Weak.
*Leaf blade tip*.—Curved downwardly.
*Leaf apex*.—Acute.
*Leaf margin*.—Serrate.
*Undulation of margin*.—Medium.
*Undulation of blade between main and lateral veins*.—Absent.
*Shape of teeth*.—Mixture of both sides straight and both sides convex.
*Length of teeth*.—Short.
*Ratio length/width of teeth*.—Small.
*Shape of upper lateral sinuses*.—Lobes slightly overlapping to lobes strongly overlapping.
*Depth of upper lateral sinuses*.—Medium.
*General shape petiole sinus*.—Half open.
*Shape of base of upper leaf sinuses*.—V-shaped.
*Tooth at petiole sinus*.—Absent.
*Density of prostrate hairs between veins on lower surface of blade*.—Absent.
*Density of erect hairs between veins on lower surface of blade*.—Very sparse.
*Density of prostrate hairs on main veins on lower surface of blade*.—Very sparse.
*Density of erect hairs on main veins on lower surface of blade*.—Medium.
*Density of prostrate hairs on main veins on upper surface of blade*.—None.
*Density of erect hairs on main veins on upper surface of blade*.—None.

*Autumn coloration of leaves*.—Leaves can be a single color or combination of colors, in a mottled pattern or on the edges of the leaves. The following colors were observed: Yellow-orange; 15A and 15B, and Orange-red: 34A, and Greyed-orange; 166C and 167A and 167B, and Greyed-red; 178A and 178B.

Upper surface:

*Color*.—The following colors were observed: Green: 137A and 137D.

*Anthocyanin coloration of main veins*.—Weak to medium.

*Coloration of main veins*.—Yellow-green: 145B.

*Surface appearance*.—Dull.

*Blistering surface of blade*.—Very weak.

Lower surface:

*Color*.—The following colors were observed: Yellow-green; 144A and 146A and 146B, and Green: 137C.

*Anthocyanin coloration of main veins* (*lower surface*).—Weak to medium.

*Color of main veins*.—Yellow-green: 145D.

*Glossiness*.—Weak.

*Surface texture*.—Smooth.

*Surface appearance*.—Dull.

Petiole:

*Length*.—About 15.7 cm.

*Diameter of petiole 2 cm from blade*.—About 3.1 mm.

*Petiole color*.—The following colors were observed: Yellow-green: 145C and Red-purple: 59A.

*Length of petiole compared to middle vein*.—Equal.

*Density of prostrate hairs on petiole*.—None.

*Density of erect hairs on petiole*.—None.

Buds:

*Bud fruitfulness*.—Basal: mostly fruitful.

*Position of first fruitful shoot on previous season cane*.—$1^{st}$ to $2^{nd}$ node.

*Dormant bud length*.—About 4.9 mm.

*Dormant bud width in the proximal/distal plane*.—About 4.9 mm.

*Dormant bud color*.—Greyed-orange: 166A.

*Time of bud burst*.—Late season: About Mar. 17, 2012.

FLOWERS

General:

*Flower sex*.—Hermaphrodite.

*Length of single flower, unopened*.—About 3.2 mm.

*Width of single flower*.—Unopened: About 1.4 mm. Opened: About 6.5 mm.

*Stamen length*.—About 2.7 mm.

*Stamen count*.—5 and 6.

*Pollen color*.—Yellow: 10B.

*Pistil length*.—About 3.0 mm.

*Pistil color*.—Yellow-green: 144A.

*Length of first inflorescence*.—Medium long: About 19.7 cm long by 10.4 cm wide.

*Position of first flowering and fruiting node*.—$2^{nd}$ to $4^{th}$ (current season growth).

*Number of inflorescence per flowering shoot*.—1.1 to 2.

*Time of bloom*.—Midseason as compared with similar varieties in the growing area of Delano, Calif.

*Date of full bloom*.—About May 15, 2012.

FRUIT

General:

*Ripening period*.—Mid-season to early: Approximately Aug. 8, 2012.

*Use*.—Fresh market.

*Keeping quality*.—Moderate, can be prone to berry shatter during handling and storage at 0° C. and high Relative humidity.

*Refractometer test*.—Soluble solids: About 16.0 Brix.

*Brix/acid*.—About 50.0.

*Titratable acidity*.—About 0.32.

*Juice ph*.—About 3.8.

Cluster:

*Mature cluster length* (*peduncle excluded*).—About 28.4 cm.

*Mature cluster width*.—About 14.6 cm.

*Mature cluster weight*.—About 859 g.

*Bunch density*.—Average.

*Number of berries*.—About 161.

*Form*.—Conical.

Peduncle:

*Lignification of peduncle*.—Weak.

*Diameter of peduncle*.—Approximately 6.5 cm.

*Length of peduncle*.—Approximately 5.3 cm.

*Color of peduncle*.—Yellow-green: 145A.

Berry:

*Uniformity of size*.—Uniform.

*Single berry weight*.—About 6.2 g natural; to about 9.6 g when treated with gibberellic acid.

*Shape*.—Elliptic.

*Seeds*.—Absent.

*Cross section*.—Circular.

*Berry dimensions*.—Longitudinal axis: About 2.9 cm horizontal axis: About 1.9 cm.

*Pedicel length*.—About 10.1 mm.

*Pedicel width*.—About 1.4 mm.

*Berry firmness*.—Firm.

*Particular flavor*.—Neutral to mild labrusca.

*Bloom* (*cuticular wax*).—Medium strong.

*Berry separation from pedicel*.—Easy.

*Skin color* (*without bloom*).—Greyed-purple: 187A and 187B.

*Flesh color*.—Yellow-green 145D.

Skin:

*Thickness*.—Medium.

*Skin toughness*.—Somewhat notable when chewing.

*Reticulation*.—Absent.

*Tenacity*.—Tenacious to flesh.

What is claimed:

1. A new and distinct variety of grapevine as herein illustrated and described.

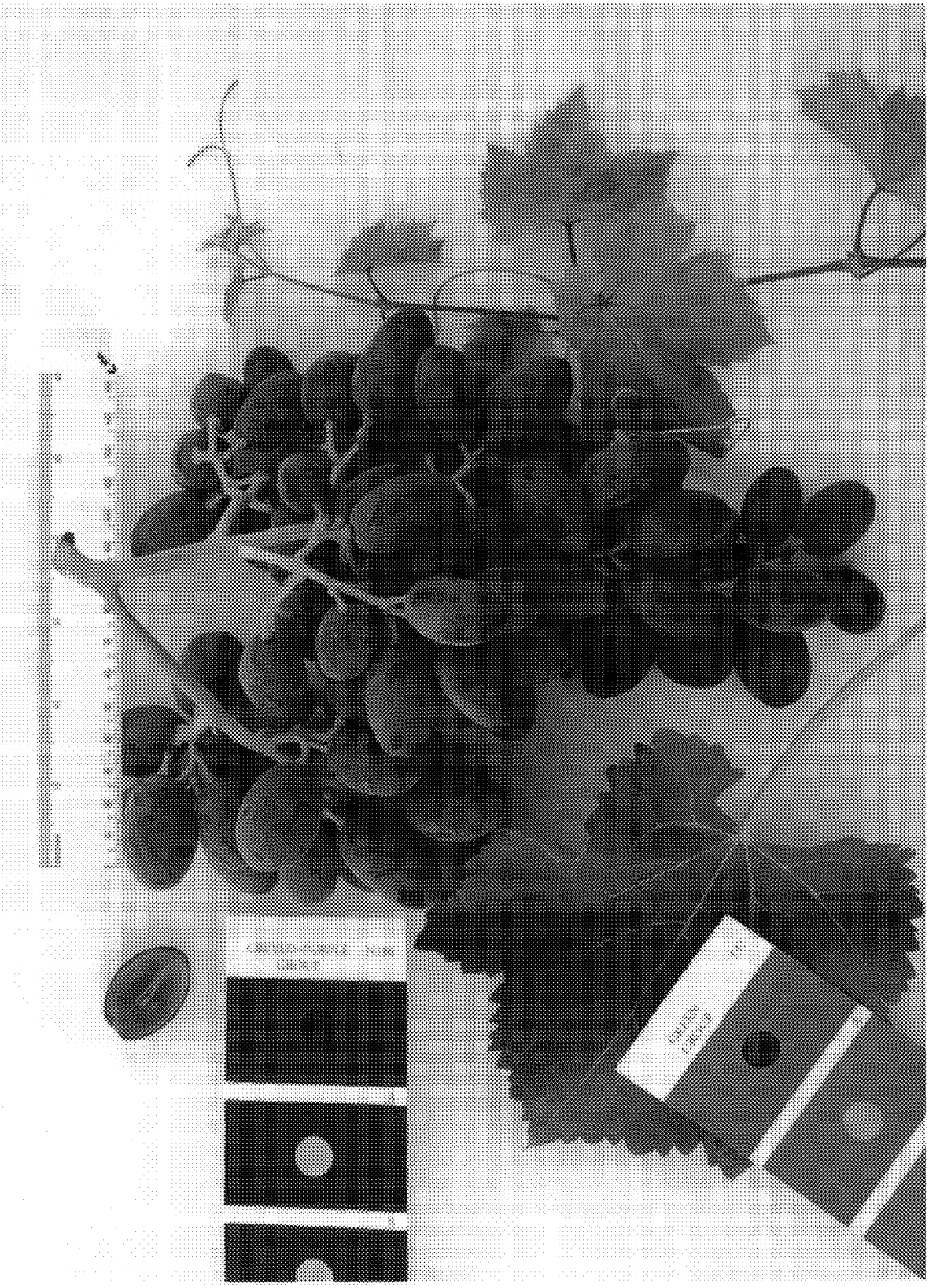

* * * * *